United States Patent
Suda et al.

(10) Patent No.: US 8,675,200 B2
(45) Date of Patent: Mar. 18, 2014

(54) HYDROGEN DETECTING SURFACE PLASMON RESONATOR, SURFACE PLASMON RESONANCE OPTICAL HYDROGEN DETECTOR AND METHOD FOR OPTICALLY DETECTING HYDROGEN USING SURFACE PLASMON RESONANCE

(75) Inventors: Atsushi Suda, Tokyo (JP); Jean-Jacques Delaunay, Tokyo (JP); Etsuo Maeda, Tokyo (JP); Ichiro Yamada, Tokyo (JP)

(73) Assignees: Japan Aviation Electronics Industry Limited, Tokyo (JP); University of Tokyo, Tokyo (JP)

(*) Notice: Subject to any disclaimer, the term of this patent is extended or adjusted under 35 U.S.C. 154(b) by 54 days.

(21) Appl. No.: 13/384,226

(22) PCT Filed: Sep. 1, 2010

(86) PCT No.: PCT/JP2010/065353
§ 371 (c)(1),
(2), (4) Date: Jan. 14, 2012

(87) PCT Pub. No.: WO2011/027899
PCT Pub. Date: Mar. 10, 2011

(65) Prior Publication Data
US 2012/0113424 A1 May 10, 2012

(30) Foreign Application Priority Data
Sep. 3, 2009 (JP) ................. 2009-203946

(51) Int. Cl.
*G01J 4/00* (2006.01)
*G01N 21/25* (2006.01)
*G01N 21/27* (2006.01)
*G01N 21/55* (2006.01)

(52) U.S. Cl.
USPC ....................... 356/445; 356/409

(58) Field of Classification Search
USPC .......... 356/445, 326, 317–318, 409; 436/164, 436/56, 34, 514; 435/287.2, 288.7; 422/50, 422/52, 55, 57, 82.11
See application file for complete search history.

(56) References Cited

U.S. PATENT DOCUMENTS 4,661,320 A * 4/1987 Ito et al. .................. 422/86
7,008,794 B2 * 3/2006 Goh et al. ................ 436/164

(Continued)

FOREIGN PATENT DOCUMENTS

| JP | 2005-265590 | 9/2005 |
| JP | 2009-053045 | 3/2009 |
| JP | 2009-150749 | 7/2009 |

OTHER PUBLICATIONS

Trouillet et al., "Fibre gratings for hydrogen sensing," Measurement Science and Technology, May 2006, vol. 17, No. 5, pp. 1124-1128.

(Continued)

*Primary Examiner* — Sang Nguyen
(74) *Attorney, Agent, or Firm* — Greenblum & Bernstein, P.L.C.

(57) ABSTRACT

Light from light source means (a wavelength-variable laser) is applied to a surface of a hydrogen absorbing thin metal film of a hydrogen detecting surface plasmon resonator including a surface plasmon resonance enhancement structure formed by providing in the thin film an array of periodic holes having a shape that is not 90-degree rotational symmetric in the plane of the film surface, and transmitted light is detected with light detecting means (a photometer). Hydrogen is detected on the basis of a change in light transmission frequency characteristic caused by hydrogen absorption in the hydrogen detecting surface plasmon resonator. Optical hydrogen detection that is highly safe and unaffected by variations in the amount of light from the light source and stray light can be achieved.

17 Claims, 7 Drawing Sheets

(56) References Cited

U.S. PATENT DOCUMENTS

| | | | |
|---|---|---|---|
| 7,522,282 B2* | 4/2009 | Nolte et al. | 356/450 |
| 7,733,491 B2* | 6/2010 | Kuroda et al. | 356/445 |
| 8,148,140 B2* | 4/2012 | Yamamichi et al. | 435/287.2 |
| 2007/0264707 A1* | 11/2007 | Liederman et al. | 435/287.2 |
| 2010/0025241 A1* | 2/2010 | Hane et al. | 204/432 |
| 2010/0053608 A1* | 3/2010 | Lee | 356/326 |
| 2010/0089123 A1* | 4/2010 | Fukui | 73/31.06 |

OTHER PUBLICATIONS

Choi et al., "Characteristics of light emission from surface plasmons based on rectangular silver gratings," Optics Communications, Jul. 2010, vol. 283, No. 14, pp. 2961-2966.

Shang et al., "Study on high speed photodectors with plasmonic filter," Proc. Asia Communications and Photonics 2009, SPIE, OSA, IEEE, Shanghai, China, Nov. 2009, vol. 7631, pp. 76311M.1-76311M.6.

Sutapun et al., "Pd-coated elastooptic fiber optic Bragg grating sensors for multiplexed hydrogen sensing," Sensors and Actuators B, Jun. 1999, vol. 60, pp. 27-34.

Maeda et al., "Analysis of hydrogen exposure effects on the transmittance of periodic sub-wavelength palladium hole arrays," Proc. SPIE, 2009, vol. 7218, pp. 72181C.1-72181C.7.

van der Molen et al., "Role of shape and localized resonances in extraordinary transmission through periodic arrays of subwavelength holes" Experiment and theory, The American Physical Society, Physical Review B, 2005, vol. 72, No. 4, pp. 045421.1-045421.9.

Eastman et al., "Narrowing of the palladium-hydrogen miscibility gap in nanocrystalline palladium," The American Physical Society, Physical Review B, Jul. 1993, vol. 48, No. 1, pp. 84-92.

Isidorsson et al., "Optical properties of $MgH_2$ measured in situ by ellipsometry and spectrophotometry," The American Physical Society, Physical Review B, 2003, vol. 68, No. 11, pp. 115112.1-115112.13.

Brolo et al., "Surface plasmon sensor based on the enhanced light transmission through arrays of nanoholes in gold films," American Chemical Society, Langmuir, 2004, vol. 20, pp. 4813-4815.

* cited by examiner

FIG. 1A  PRIOR ART
FIG. 1B  PRIOR ART
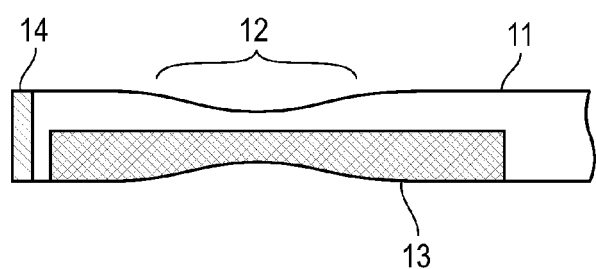
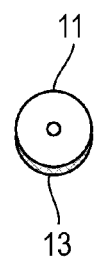
FIG. 2  PRIOR ART
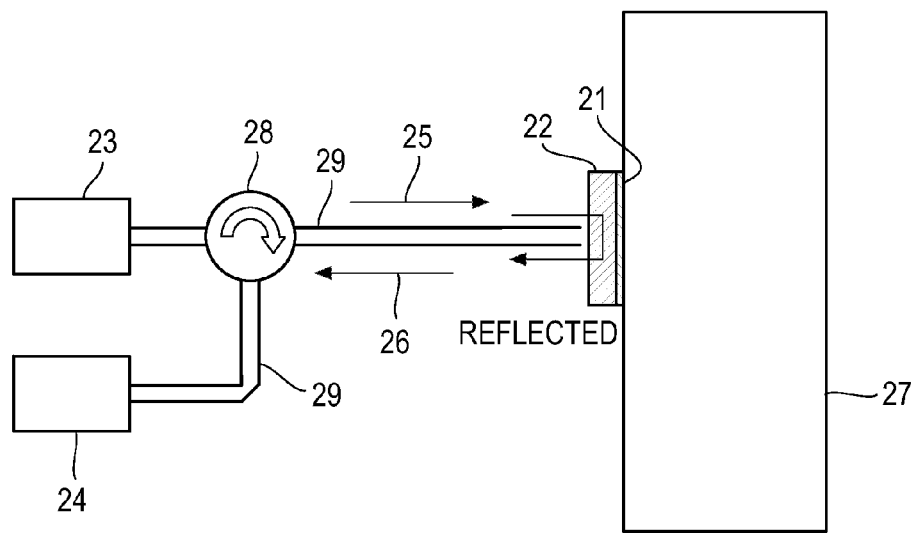

HYDROGEN DETECTING SURFACE PLASMON RESONATOR, SURFACE PLASMON RESONANCE OPTICAL HYDROGEN DETECTOR AND METHOD FOR OPTICALLY DETECTING HYDROGEN USING SURFACE PLASMON RESONANCE

TECHNICAL FIELD

The present invention relates to a hydrogen detector and a method for detecting hydrogen and, in particular, to an optical hydrogen detector and a method for optically detecting hydrogen that use a surface plasmon resonator.

BACKGROUND ART

Use of hydrogen as a new energy source has come to attention in recent years. Due to safety concerns and poor public perceptions about hydrogen, one of the most important issues in advancing the hydrogen-based industries is development of highly reliable hydrogen detection techniques.

Conventionally used hydrogen detection means are mostly catalytic combustion type and semiconductor type. The former causes a heated thin line of platinum or palladium to react with hydrogen to detect variations in electric conductivity; the latter provides an electrode pair in a layer of an oxide semiconductor such as tin oxide on a substrate to detect an increase in the number of carriers in the semiconductor layer due to contact with hydrogen. However, these approaches have a drawback that they entail the danger of ignition because there is an electric contact in a sensor part, thereby requiring explosion protection means.

On the other hand, several approaches to detecting hydrogen by using an all-optical sensor part have been studied. The approaches do not have the drawback described above and have the advantage of a high level of safety.

For example, Patent literature 1 describes a technique in which a hydrogen absorbing film is formed in a constricted portion of an optical fiber and expansion of the volume of the hydrogen absorbing film changes bending loss that occurs in the constricted portion of the optical fiber. FIGS. 1A and 1B illustrates a configuration of a sensor part of a hydrogen sensor described in Patent literature 1. In the figures, 11 denotes an optical fiber, 12 denotes a constricted portion of the optical fiber 11 which is a narrowed portion of the optical fiber 11, 13 denotes a hydrogen absorbing film, and 14 denotes a reflecting mirror which reflects measurement light that entered the optical fiber 11. In this example, a change in the intensity of reflected light is detected to detect hydrogen.

Patent literature 2 describes a technique which uses a hydrogen sensitive switchable mirror to detect a change in light reflectance and transmittance. FIG. 2 illustrates a configuration of a hydrogen sensor described in Patent literature 2. The hydrogen sensor includes a probe 22 with a hydrogen sensitive switchable mirror 21 disposed to be exposed to an atmosphere of interest 27, a light source 23 which emits probe light 25 toward the probe 22, a photodetector 24 which receives detection light 26 reflected by the probe 22, and an optical waveguide 29 having one end disposed close to the probe 22 and the other end connected to the light source 23 and the photodetector 24 through an isolator 28. In this example, the intensity of the detection light 26 can be monitored with the photodetector 24 to detect presence or absence of hydrogen in the atmosphere of interest 27 and the concentration of hydrogen in the atmosphere of interest 27.

On the other hand, Non-patent literature 1 describes a technique which uses a surface plasmon resonator configured with periodic holes formed in a thin film of palladium, which is a hydrogen absorbing metal, to detect a decrease in the amount of transmitted light due to absorption of hydrogen by the thin film.

PRIOR ART LITERATURE

Patent Literatures:
  Patent literature 1: Japanese Patent Application Laid-Open No. 2009-53045
  Patent literature 2: Japanese Patent Application Laid-Open No. 2005-265590
Non-Patent Literature:
  Non-patent literature 1: E. Maeda, et al., "Analysis of hydrogen exposure effects on the transmittance of periodic sub-wavelength palladium hole arrays", Proc. of SPIE, Vol. 7218, 72181C, 2009

SUMMARY OF THE INVENTION

Problems to be Solved by the Invention

For safety reasons, it is preferable to use optical means in detection of hydrogen. The techniques described in Patent literatures 1 and 2 and the technique described in Non-patent literature 1 given above use different methods but are the same in that hydrogen is detected on the basis of changes in the amount of transmitted or reflected light in some element that is sensitive to hydrogen. That is, the principles of the existing optical hydrogen detection techniques are based on changes in the amount of light.

However, such detection methods based on changes in the amount of transmitted or reflected light have an inherent shortcoming that detection errors are caused by variations in the amount of light from the light source and stray light and have a problem that the influences of the variations and stray light cannot completely be eliminated.

The present invention has been made in light of these circumstances and an object of the present invention is to provide an all-optical-sensor-based, safe optical hydrogen detection technique that is robust and unaffected by variations in the amount of light from a light source and stray light because the technique is based on observation of what is inherently different from changes in the amount of transmitted or reflected light.

Means to Solve the Problems

According to the present invention, a hydrogen detecting surface plasmon resonator includes an array of periodic holes provided in a thin film of a hydrogen absorbing metal to form a surface plasmon resonance enhancement structure, wherein the holes have a shape that is not 90-degree rotationally symmetric in a plane of a surface of the thin film.

According to the present invention, a surface plasmon resonance optical hydrogen detector includes: a hydrogen detecting surface plasmon resonator including an array of periodic holes provided in a thin film of a hydrogen absorbing metal to form a surface plasmon resonance enhancement structure, the holes having a shape that is not 90-degree rotationally symmetric in a plane of a surface of the thin film; and light source means for illuminating the film surface of the hydrogen detecting surface plasmon resonator with light; and light detecting means for detecting light transmitted through the hydrogen detecting surface plasmon resonator with respect to light from the light source means; wherein hydrogen is detected on the basis of a change in a light transmission frequency characteristic caused by hydrogen absorption by the hydrogen detecting surface plasmon resonator.

According to the present invention, a method for optically detecting hydrogen by using surface plasmon resonance illuminates, with light from light source means, a film surface of a hydrogen detecting surface plasmon resonator including an array of periodic holes provided in a thin film of a hydrogen absorbing metal to form a surface plasmon resonance enhancement structure, the holes having a shape that is not 90-degree rotationally symmetric in the plane of the thin film and detects, by light detecting means, light transmitted through the hydrogen detecting surface plasmon resonator with respect to the illumination with the light, wherein hydrogen is detected on the basis of a change in a light transmission frequency characteristic caused by hydrogen absorption by the hydrogen detecting surface plasmon resonator.

[Operation]

The effects that the present invention uses in the principal part are: an Extra Transmission Effect in an array of periodic holes in a metal thin film, which is one mode of a surface plasmon resonance enhancement structure, an effect of a specific shape of holes on the extraordinary transmission effect, and expansion and changes in an optical property caused by hydrogenation of a hydrogen absorbing metal.

Firstly, the extraordinary transmission effect is a phenomenon in which coupling of incident light with surface plasmon polaritons on the surface of a metal thin film in which an array of periodic subwavelength holes are provided allows the light to be transmitted through the subwavelength holes at characteristic wavelengths. The coupling (resonance) of light incident on the surface of the metal with surface plasmons is enhanced by what is called a surface plasmon resonance enhancement structure, in which periodic projections and depressions or holes are provided in the surface of the metal to make resonance properties steeper. If the structure includes holes smaller than the wavelength of light, the light passes through the holes with an extraordinary intensity at a resonance wavelength. The peak wavelength of the resonance transmission corresponds to a point at which the momentum of the surface plasmons and the momentum of the incident photons match each other.

Secondly, it is known that holes having a shape that has a so-called aspect ratio, such as a rectangle or an ellipse, change the intensity and frequency characteristics of transmitted light as a function of the direction of polarization of applied light and that the way of the change varies with the aspect ratio. In particular, it was observed that when linearly polarized light is applied along the shorter axis that makes up the aspect ratio of holes (the shorter dimension of the holes along a linear direction), peak wavelengths of transmission light spectra changes nearly linearly as a function of the aspect ratio (K. L. van der Molen, et al., "Role of shape and localized resonances in extraordinary transmission through periodic arrays of subwavelength holes: Experiment and theory", Physical Review B72, 045421, 2005). This is the effect of a specific shape of holes on the extraordinary transmission effect that the present invention uses.

Thirdly, it is known that when a hydrogen absorbing metal such as palladium is hydrogenated upon expose to hydrogen, expansion of the crystalline lattice (J. A. Eastman, et al., "Narrowing of the palladium-hydrogen miscibility gap in nanocrystalline palladium", Physical Review B, Volume 48, Number 1, 1993) and a change in optical properties (J. Isidorsson, et al., "Optical properties of $MgH_2$ measured in situ by ellipsometry and spectrophotometry", Physical Review B 68, 115112, 2003) occur. Here, if the above-described array of holes having an aspect ratio is made of the hydrogen absorbing metal, the aspect ratio of the holes changes due to lattice expansion with a change in the optical properties when the hydrogen absorbing metal reacts with hydrogen. The present invention shows that the two effects, namely the change in the aspect ratio and the change in the optical properties caused by hydrogenation cause a shift of the peak wavelength of transmitted light in the same direction, and has successfully achieved highly sensitive detection of hydrogen by using the combination of these effects.

Effects of the Invention

The present invention can provide an all-optical-sensor-based, safe optical hydrogen detection technique that is highly sensitive to hydrogen, and robust and unaffected by variations in the amount of light from a light source and stray light because the detection is based on observation of changes in an optical frequency characteristic.

BRIEF DESCRIPTION OF THE DRAWINGS

FIG. 1A is a front view illustrating an exemplary configuration of a conventional hydrogen detector (hydrogen sensor);

FIG. 1B is a side view of the hydrogen detector in FIG. 1A;

FIG. 2 is a diagram illustrating another exemplary configuration of a conventional hydrogen detector (hydrogen sensor);

DETAILED DESCRIPTION OF THE EMBODIMENTS

The present invention provides a configuration of new means for detecting hydrogen based on wavelength shifts in a main resonance mode of an array of sub-wavelength rectangular metal holes that exhibit an extraordinary transmission effect. Attempts have been widely made to use surface plasmon resonance for detecting biological and chemical substances in the past. Such exiting techniques change optical properties of a metal-air interface by absorption of biological/chemical substances on the surface of the metal (for example, A. G. Brolo, et al., "Surface Plasmon Sensor Based on the Enhanced Light Transmission through Arrays of Nanoholes in Gold Films", Langmuir, 20, 12, 4812, 2004). In the present invention, in contrast, an array of holes in a metal itself changes upon exposure to hydrogen.

An implementation that uses palladium as a hydrogen absorbing metal will be described below.

It is formation of a palladium hydride phase upon exposure to hydrogen that causes wavelength shifts in the main resonance mode in surface plasmon resonance. The formation of the palladium hydride phase effects a change in the permittivity of a palladium hole array and an increase in the aspect ratio of rectangular holes due to palladium lattice expansion. Results of simulations performed concurrently with fabrication of embodiments show that changes in both of the permittivity and shape of holes cause a wavelength shift toward longer wavelengths and in fact the changes cause observed large wavelength shifts.

First Embodiment

Figures 3A, 3B:
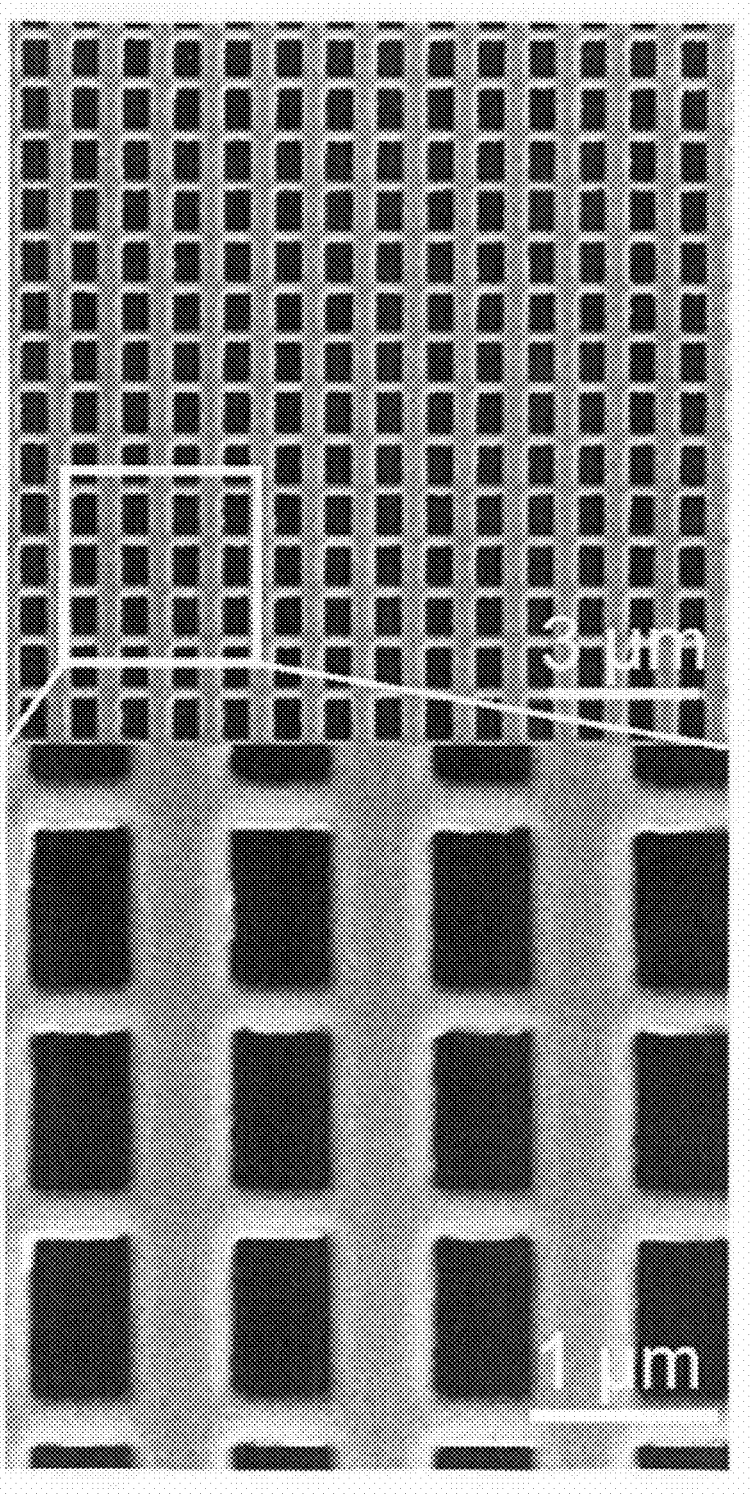
FIG. 3A is a photograph showing an exemplary configuration of a surface plasmon resonator for detecting hydrogen according to the present invention.
FIG. 3B is an enlarged photograph of a portion enclosed in a box in FIG. 3A.

FIGS. 3A and 3B illustrate an example of a subwavelength palladium hole array fabricated as a hydrogen detecting surface plasmon resonator according to the present invention.

In this example, in total six subwavelength palladium hole arrays having slightly different hole dimensions were fabricated by direct-write electron beam lithography on a silicon substrate according to a fabrication procedure illustrated in FIGS. 4A to 4D.

Figure 4A:
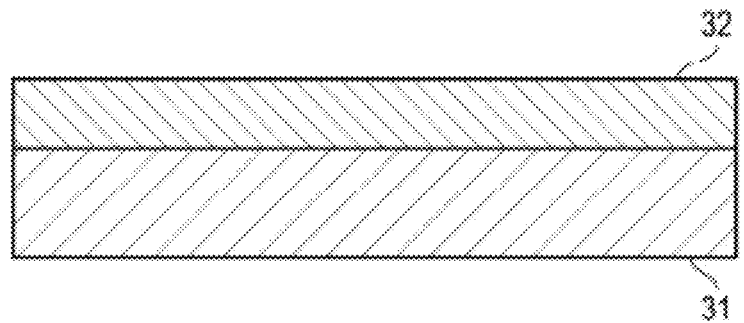
FIG. 4A is a diagram illustrating a first step of the process of fabricating the hydrogen detecting surface plasmon resonator illustrated in FIG. 3A.
Figure 4B:
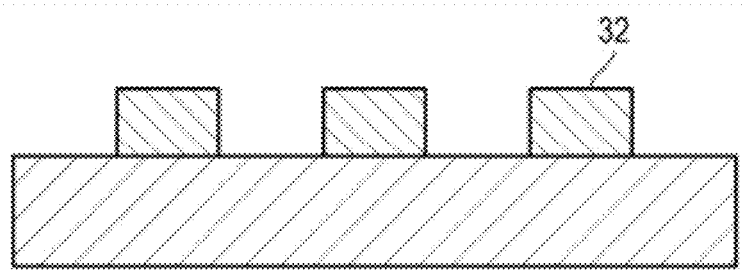
FIG. 4B is a diagram illustrating a step following the step in FIG. 4A.
Figure 4C:
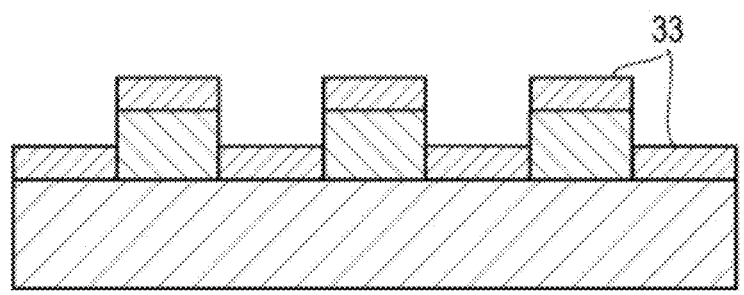
FIG. 4C is a diagram illustrating a step following the step in FIG. 4B.
Figure 4D:
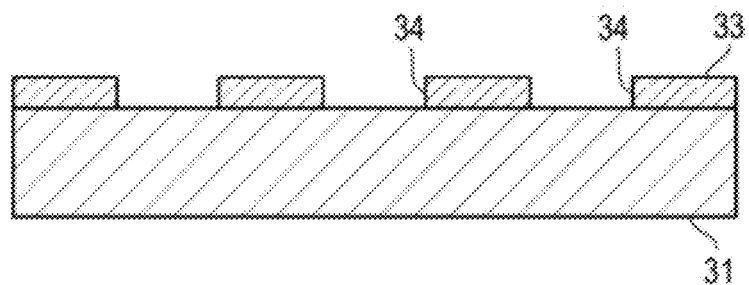
FIG. 4D is a diagram illustrating a step following the step in FIG. 4C.

The desired periodic feature was obtained by applying direct electron beam writing to a 400-nm-thick resist 32 spin-coated on a silicon substrate 31 (FIG. 4A) and developing the resist 32 (FIG. 4B). A 100-nm-thick palladium thin film 33 is deposited on the resist pattern by sputtering (FIG. 4C) and finally the resist 32 is removed by a lift-off process to fabricate an array of periodic holes 34 (FIG. 4D).

All holes are rectangular in shape and all of the six subwavelength palladium hole arrays were square arrays with an identical 1.1 μm lattice period in the two orthogonal directions.

The dimensions (along a longer axis and a shorter axis in μm) of each rectangular hole of the six subwavelength palladium hole arrays were (0.80, 0.80), (0.80, 0.70), (0.80, 0.60), (0.80, 0.50), (0.80, 0.40), and (0.80, 0.30) and aspect ratios were 1.0, 1.1, 1.3, 1.6, 2.0 and 2.6, respectively. The dimensions of the holes were estimated from field emission scanning electron microscope images.

Figure 5:
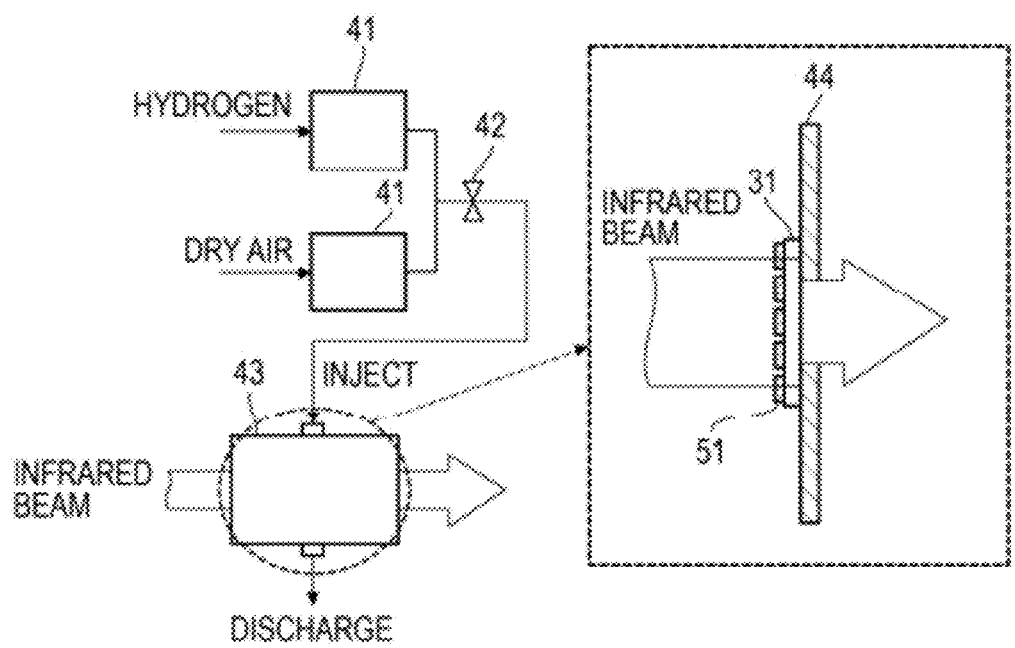
FIG. 5 is a diagram for explaining a configuration of a first embodiment of a surface plasmon resonance optical hydrogen detector according to the present invention.

The extraordinary transmission effect of the fabricated subwavelength palladium hole arrays was observed using an apparatus illustrated in FIG. 5. In FIG. 5, reference numeral 41 denotes a mass flow controller, 42 denotes a valve, and 43 denotes a gas chamber. A subwavelength palladium hole array 51 is placed on an aperture 44 in the gas chamber 43.

Figure 6A:
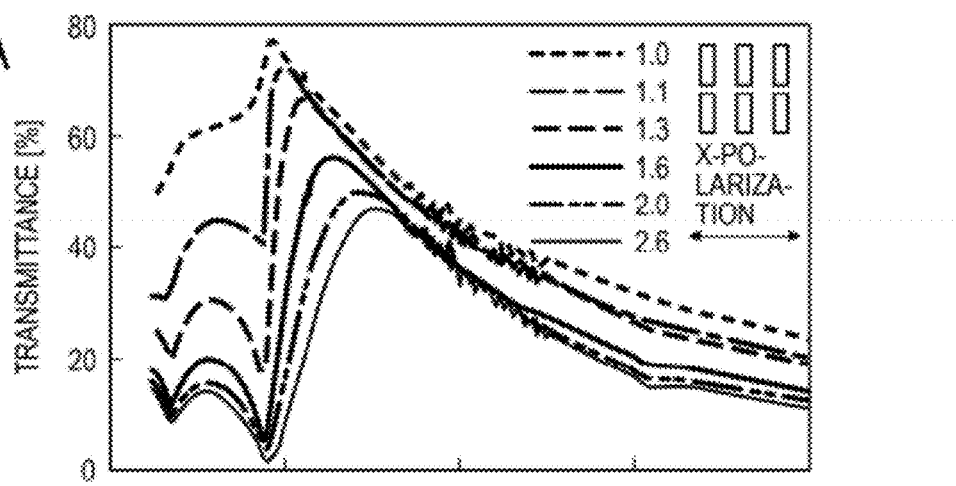
FIG. 6A is a graph of curves of measured transmittance spectra with different aspect ratios of holes.

Light (an infrared beam) was applied perpendicularly from a light source with a wide wavelength band in the infrared range, not shown, to the film surface of the subwavelength palladium hole array 51. The light was linearly polarized in a polarization direction across the longer sides of the rectangular holes, that is, parallel to the shorter axis, as illustrated in FIG. 6A, because linearly polarized light aligned with the shorter axis is known to maximize the effect of resonance peak shifts for holes having an aspect ratio (the forecited paper by K. L. van der Molen et al.).

Transmitted light is received by a spectrometer, not shown. A Fourier transform infrared spectrometer was used in this example to obtain zero-order transmission spectra in the wavelength band of 2.5 to 10 μm with a resolution of 2 nm. The configuration of the surface plasmon resonance optical hydrogen detector in this embodiment has been described in the foregoing.

Figure 6B:
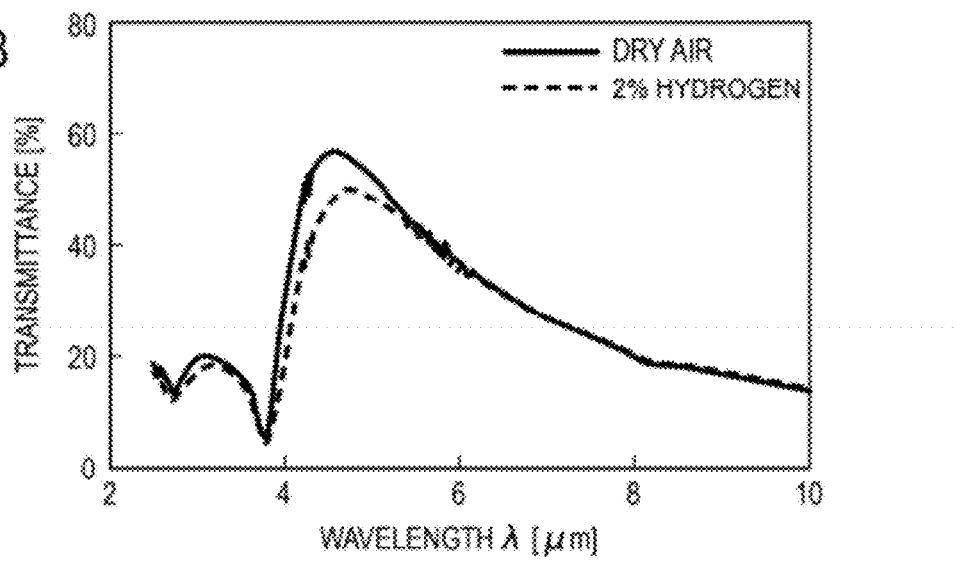
FIG. 6B is a graph of results of observations of changes in transmittance spectra due to exposure to 2% hydrogen at an aspect ratio of 1.6.

FIG. 6A shows observed transmission spectra of the subwavelength palladium hole arrays with different aspect ratios in dry air in this embodiment. The main resonance peak (wavelengths between 4 and 5 μm, corresponding to (1, 0) propagation mode of the arrays) shifts toward longer wavelengths as the aspect ratio increases. FIG. 6B shows the effect of hydrogen exposure on the transmission spectrum of the array that has an aspect ratio of 1.6. It can be seen that a 200 nm shift of the main resonance peak toward longer wavelengths is caused by hydrogen exposure.

For comparison with observation results described above, propagation of an electromagnetic wave passing through subwavelength palladium hole arrays was simulated using a Rigorous Coupled-Wave Analysis (hereinafter abbreviated as "RCWA") method.

Figure 7A:
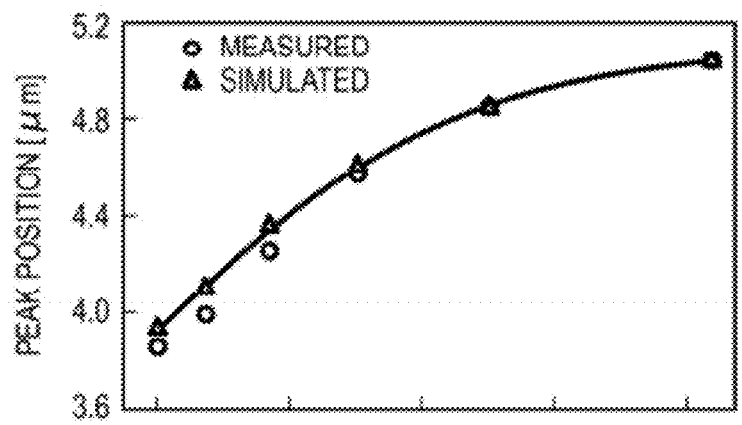
FIG. 7A is a graph of measured values of changes in peak position in Pd/Si (1, 0) mode as a function of the aspect ratio of rectangular holes and results of a simulation.

In the RCWA simulation, frequency dependence of the relative permittivities of palladium and silicon was represented by Drude's functions. FIG. 7A shows calculated and measured positions of the (1, 0) resonance mode for different aspect ratios. The simulated peak positions are in good agreement with the measured positions. Therefore, it can be said that the effect of the hole shape is correctly reproduced by the RCWA simulation.

The RCWA simulation was then used to simulate the effect of reaction of the subwavelength palladium hole array to hydrogen in the following way. Hydrogen absorption by palladium produces a palladium hydride phase, which decreases the absolute values of the real and imaginary parts of the permittivity of palladium and causes expansion of the volume of the original palladium lattice. Here, change in optical properties of the palladium layer was simulated by a decrease in the absolute value of the permittivity of palladium taken as 20%. Change in the dimensions of the hole array was simulated by a 3.5% expansion of the palladium lattice. The value represents full expansion at the alpha-to-beta phase transition of the palladium lattice near 2% hydrogen.

Figure 7B:
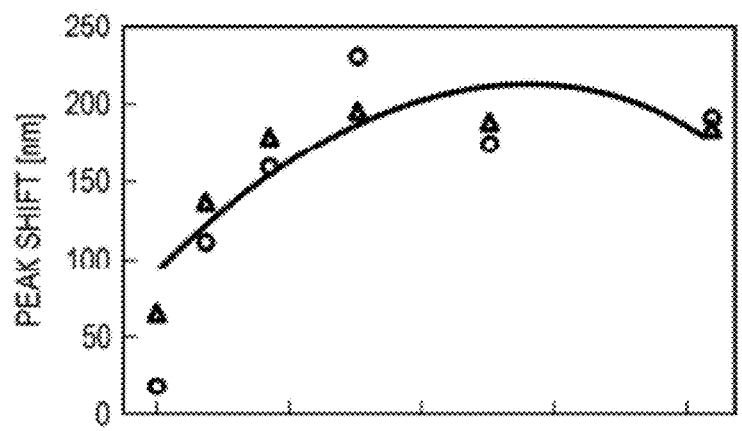
FIG. 7B is a graph of measured values of a (1, 0) peak shift due to exposure to 2% hydrogen and results of a simulation.

FIG. 7B shows observed shifts of the main resonance peak of the fabricated series of the subwavelength palladium hole arrays when exposed to 2% hydrogen, together with the results of the simulation described above. The good agreement between the observed and simulated peak shifts over the investigated range of aspect ratios is evidence that the simulation method correctly represents the effect of hydrogen absorption on the subwavelength palladium hole arrays. It should be noted not only that the peak shift saturates at aspect ratios of 1.6 and greater but also that the absolute values of the shift are in good agreement with experimental values.

Figure 7C:
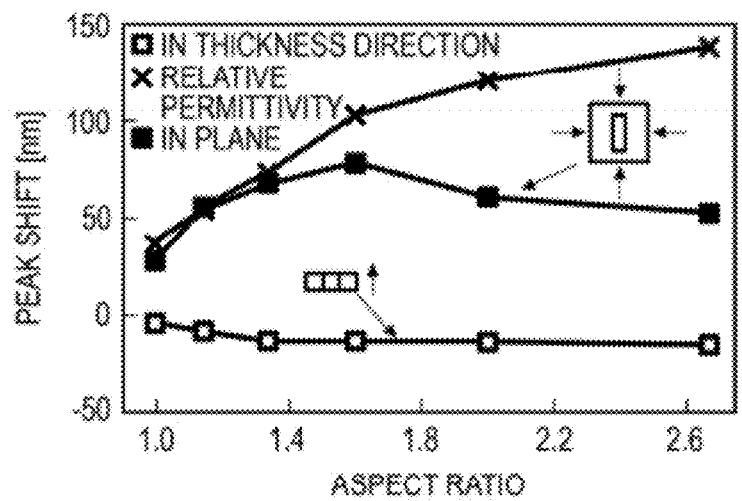
FIG. 7C is a graph of results of simulations of contributions of three factors, namely a change (a 20% decrease of the absolute values of real/imaginary parts) of relative permittivity of a palladium layer, expansions (3.5%) in a film surface and in the direction of thickness of the layer, induced by exposure to 2% hydrogen.

Different factors that contribute to the peak shift were simulated independently. Their contributions to the total shift are shown in FIG. 7C. The decrease in the absolute value of the relative permittivity induces an increase in the resonance wavelength, which has a significant contribution to the total shift. Palladium expansion results in expansion of the lattice, which translates into a decrease in the dimensions of the holes and vertical expansion, that is, an increase in the thickness. These have opposite effects on the peak shift. The expansion of the lattice increases the aspect ratio of the rectangular holes and therefore causes a peak shift toward longer wavelengths, whereas the vertical expansion caused by the increase in the thickness of the palladium layer is thought to have a sufficiently small effect on the peak position for a thickness of the layer of 100 nm considered here. The optimum aspect ratio at which the largest wavelength shift was obtained with a constant rectangle length was found to be 1.6.

Thus, the novel hydrogen detection method based on shifts of the resonance peak of subwavelength palladium rectangular hole arrays has been validated by both experimental and numerical analyses. The RCWA simulations have revealed that the large peak shift is caused by the combined effects of a change in the permittivity of palladium and a change in the hole shape, which add up to generation of the large wavelength shifts. An optimum aspect ratio that increases the peak shift was found, at which a peak shift as large as 200 nm was observed upon exposure to 2% hydrogen.

Because the all-optical hydrogen detector and detection method proposed by the present invention is fully selective to hydrogen, the hydrogen detector and detection method are useful in applications where gas selectivity is an issue.

Second Embodiment

Figure 8:
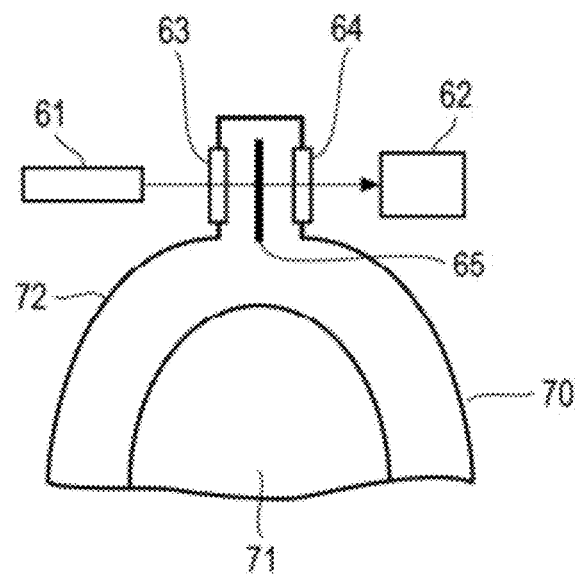
FIG. 8 is a diagram for explaining a configuration of a second embodiment of a surface plasmon resonance optical hydrogen detector according to the present invention.

FIG. 8 illustrates a second embodiment of a surface plasmon resonance optical hydrogen detector according to the present invention.

Light source means and light detection means used in this embodiment are a wavelength-variable laser 61 and a photometer 62, respectively. Peak wavelength shifts of transmitted light can be observed by this method as well, of course.

Specifically, the surface plasmon resonance optical hydrogen detector of this embodiment includes a built-in hydrogen storage part 71 which is attached across an outer wall 72 of a device 70 configured to monitor leakage of hydrogen inside it. That is, two optical windows (an incident optical window 63 and an exit optical window 64) that function as a light incident port and a light exit port, respectively, are provided on the outer wall 72 as illustrated in FIG. 8. A hydrogen detecting surface plasmon resonator 65 is disposed in an inner part of the device 70 that is within the outer wall 72, whereas the wavelength-variable laser 61 and the photometer 62 which are to be connected to an electrical system, are disposed in locations outside the device 70 where leak hydrogen does not reach, thereby ensuring safety.

Third Embodiment

A variation of the second embodiment described above is illustrated in FIG. 9 as a third embodiment.

Figure 9:
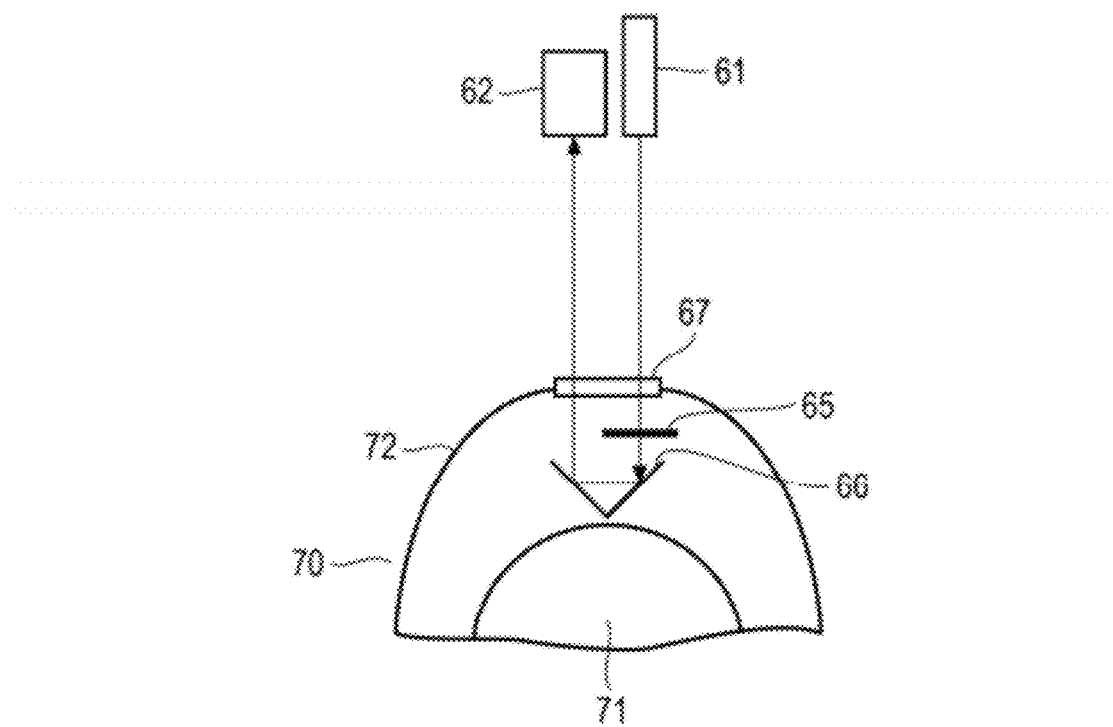
FIG. 9 is a diagram for explaining a configuration of a third embodiment of a surface plasmon resonance optical hydrogen detector according to the present invention.

In the second embodiment, projecting parts are formed for providing on the outer wall the two opposed optical windows with a hydrogen detecting surface plasmon resonator between them for the purpose of detecting light transmitted through the hydrogen detecting surface plasmon resonator. The third embodiment does not need such modifications to the shape of the outer wall and is creatively designed so that a single optical window that functions as a light incident and exit port will suffice. Specifically, as illustrated in FIG. 9, a right-angled mirror 66, which is mirror means for reflecting transmitted light in the opposite direction, is disposed in an inner part of a device 70 within an outer wall 72, together with a hydrogen detecting surface plasmon resonator 65. Light transmitted through the hydrogen detecting surface plasmon resonator 65 travels in the opposite direction through the same optical window (the incident and exit optical window 67) through which light from a light source (a wavelength-variable laser 61) traveled and is guided to the outside.

While the embodiments described above use palladium as the hydrogen absorbing metal of the hydrogen detecting surface plasmon resonator, other metal such as a palladium alloy, a lanthanum-nickel alloy, a rare-earth-metal-nickel alloy or a magnesium-nickel alloy may be used.

While the holes of the hydrogen detecting surface plasmon resonators in the embodiments described above are rectangular, the holes may have any other shape that is not 90-degree rotationally symmetric and has a difference between two dimensions projected in any of the orthogonal directions in a plane, such as an ellipse or an oval.

Furthermore, the array of the holes is not limited to a square, lattice-shaped arrangement having identical periodicity in two orthogonal directions as in the embodiment described above; the array may have periodicity defined by a combination of vectors that are not orthogonal to each other and/or are different in magnitude.

Moreover, illumination of the film surface of the hydrogen detecting surface plasmon resonator with light does not necessarily need to be vertical incidence. Optimum illuminating light is linearly polarized light with the orientation of the polarization plane aligned with the direction along the shorter one of the orthogonal axes that form the aspect ratio of holes, that is, in the direction along the shorter one of the dimensions of holes. However, light polarized in other direction, or circularly polarized light or unpolarized light can be used to implement hydrogen detection of the present invention.

What is claimed is:

1. A hydrogen detecting surface plasmon resonator comprising
   a thin film of a hydrogen absorbing metal, and
   an array of periodic holes fabricated in an area of the thin film to form a surface plasmon resonance enhancement structure, a surface of the area of the thin film being exposed to hydrogen,
   wherein the holes have a shape that is not 90-degree rotationally symmetric in a plane of a surface of the thin film.

2. The hydrogen detecting surface plasmon resonator according to claim 1, wherein the hydrogen absorbing metal is palladium.

3. The hydrogen detecting surface plasmon resonator according to claim 1, wherein:
   the shape of each of the holes is a rectangle having a shorter side and a longer side; and
   the rectangular holes of the array of periodic holes are periodically arranged along two directions orthogonal to each other, one of the directions being parallel to the shorter side and the other being parallel to the longer side.

4. A surface plasmon resonance optical hydrogen detector comprising:
   a hydrogen detecting surface plasmon resonator comprising a thin film of a hydrogen absorbing metal and an array of periodic holes fabricated in an area of the thin film to form a surface plasmon resonance enhancement structure, a surface of the area of the thin film being exposed to hydrogen, wherein the holes have a shape that is not 90-degree rotationally symmetric in a plane of a surface of the thin film;
   a light source for illuminating the film surface of the hydrogen detecting surface plasmon resonator with light; and
   a light detector for detecting light transmitted through the hydrogen detecting surface plasmon resonator with respect to light from the light source;

wherein hydrogen is detected on the basis of a change in a light transmission frequency characteristic caused by hydrogen absorption by the hydrogen detecting surface plasmon resonator.

5. The surface plasmon resonance optical hydrogen detector according to claim 4,
wherein the light from the light source illuminating the film surface of the hydrogen detecting surface plasmon resonator is linearly polarized light and the orientation of the polarization plane is aligned with a linear direction such that the ratio of a projected dimension of the holes to a dimension projected in a direction orthogonal to the dimension is minimized in the plane of the surface of the hydrogen detecting surface plasmon resonator.

6. The surface plasmon resonance optical hydrogen detector according to claim 4, wherein the hydrogen absorbing metal of the hydrogen detecting surface plasmon resonator is palladium.

7. The surface plasmon resonance optical hydrogen detector according to claim 4, wherein:
each of the holes of the hydrogen detecting surface plasmon resonator is a rectangular hole with a shorter side and a longer side; and
the rectangular holes of the array of periodic holes are periodically arranged along two directions orthogonal to each other, one of the directions being parallel to the shorter side and the other being parallel to the longer side or each rectangular hole.

8. The surface plasmon resonance optical hydrogen detector according to claim 4, wherein:
the light source is a wavelength-variable laser; and
the light detector is a photometer.

9. The surface plasmon resonance optical hydrogen detector according to claim 4, wherein:
the light source is a wide-wavelength-band light source; and
the light detector is a spectrometer.

10. The surface plasmon resonance optical hydrogen detector according to claim 4, wherein:
the hydrogen detecting surface plasmon resonator is disposed inside a closed space in which hydrogen gas is to be detected, the closed space being enclosed with an outer wall;
the light source and the light detector are disposed outside the closed space;
an incident optical window and an exit optical window are provided at locations on the outer wall that are opposed to each other with the hydrogen detecting surface plasmon resonator between the locations; and
the surface plasmon resonance optical hydrogen detector is configured so that light from the light source travels through the incident optical window to illuminate the hydrogen detecting surface plasmon resonator and light transmitted through the hydrogen detecting surface plasmon resonator travels through the exit optical window to reach the light detector.

11. The surface plasmon resonance optical hydrogen detector according to claim 4, wherein:
the hydrogen detecting surface plasmon resonator and a minor are disposed inside a closed space in which hydrogen gas is to be detected, the closed space being enclosed with an outer wall; and
the light source and the light detector are disposed outside the closed space;
an incident and exit optical window is provided on the outer wall; and
the surface plasmon resonance optical hydrogen detector is configured so that light from the light source travels through the incident and exit optical window to illuminate the hydrogen detecting surface plasmon resonator and light transmitted through the hydrogen detecting surface plasmon resonator is reflected by the minor and travels through the incident and exit optical window in the indirection opposite to the travel of the light from the light source to reach the light detector.

12. A method for optically detecting hydrogen by using surface plasmon resonance, comprising:
illuminating, with light from a light source, a film surface of a hydrogen detecting surface plasmon resonator including an array of periodic holes provided in a thin film of a hydrogen absorbing metal to form a surface plasmon resonance enhancement structure, the holes having a shape that is not 90-degree rotationally symmetric in the plane of the thin film; and
detecting, by a light detector, light transmitted through the hydrogen detecting surface plasmon resonator with respect to the illumination with the light;
wherein hydrogen is detected on the basis of a change in a light transmission frequency characteristic caused by hydrogen absorption by the hydrogen detecting surface plasmon resonator.

13. The method for optically detecting hydrogen by using surface plasmon resonance according to claim 12, wherein:
light from the light source illuminating the film surface of the hydrogen detecting surface plasmon resonator is linearly polarized light and the orientation of the polarization plane is aligned with a linear direction such that the ratio of a projected dimension of the holes to a dimension projected in a direction orthogonal to the dimension is minimized in the plane of the surface of the hydrogen detecting surface plasmon resonator.

14. The method for optically detecting hydrogen by using surface plasmon resonance according to claim 12, wherein the hydrogen absorbing metal of the hydrogen detecting surface plasmon resonator is palladium.

15. The method for optically detecting hydrogen using surface plasmon resonance according to claim 12, wherein:
each of the holes of the hydrogen detecting surface plasmon resonator is a rectangular hole having a shorter side and a longer side; and
the rectangular holes of the array of periodic holes are periodically arranged along two directions orthogonal to each other, one of the directions being parallel to the shorter side and the other being parallel to the longer side of each rectangular hole.

16. The method for optically detecting hydrogen by using surface plasmon resonance according to claim 12, wherein:
the light source is a wavelength-variable laser; and
the light detector is a photometer.

17. The method for optically detecting hydrogen by using surface plasmon resonance according to claim 12, wherein:
the light source is a wide-wavelength-band light source; and
the light detector is a spectrometer.

* * * * *

UNITED STATES PATENT AND TRADEMARK OFFICE
CERTIFICATE OF CORRECTION

| | |
|---|---|
| PATENT NO. | : 8,675,200 B2 |
| APPLICATION NO. | : 13/384226 |
| DATED | : March 18, 2014 |
| INVENTOR(S) | : A. Suda et al. |

It is certified that error appears in the above-identified patent and that said Letters Patent is hereby corrected as shown below:

On the Title Page, under (73) Assignees, of the printed patent, "University of Tokyo, Tokyo (JP)" should read --The University of Tokyo, Tokyo (JP)--.

Signed and Sealed this
Second Day of September, 2014

Michelle K. Lee
*Deputy Director of the United States Patent and Trademark Office*